(12) United States Patent
Wong et al.

(10) Patent No.: US 8,329,425 B2
(45) Date of Patent: Dec. 11, 2012

(54) METHOD AND SYSTEM FOR DETECTION OF CHLORAMPHENICOL

(75) Inventors: Kwok-Yin Wong, Hong Kong (CN); Yun Chung Leung, Hong Kong (CN); Pak Ho Chan, Hong Kong (CN); Wai Hong Chung, Hong Kong (CN); Ka Yan Chow, Hong Kong (CN); Ho yin Chow, Hong Kong (CN); Hon Man Leung, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 0 days.

(21) Appl. No.: 13/036,021

(22) Filed: Feb. 28, 2011

(65) Prior Publication Data

US 2012/0219978 A1 Aug. 30, 2012

(51) Int. Cl.
*C12Q 1/48* (2006.01)
*C12N 9/10* (2006.01)

(52) U.S. Cl. .......................................... 435/15; 435/193
(58) Field of Classification Search .................. None
See application file for complete search history.

(56) References Cited

U.S. PATENT DOCUMENTS

| | | | |
|---|---|---|---|
| 4,420,568 A | 12/1983 | Wang et al. | |
| 5,262,545 A | 11/1993 | Haughland et al. | |
| 5,364,764 A | 11/1994 | Haughland et al. | |
| 6,225,074 B1 | 5/2001 | Wright et al. | |

OTHER PUBLICATIONS

Ellis et al. Intrinsic fluorescence of chloramphenicol acetyltransferase . . . Biochemistry (1991) 30 (30), 10799-10805.*
Marmé, N., et al; "Inter- and Intramolecular Fluorescence Quenching of Organic Dyes by Tryptophan," *Bioconjugate Chemistry 2003*; 14(6); pp. 1133-1139.
Marmé, N., et al; "Highly Sensitive Protease Assay Using Flourescence Quenching of Peptide Probes Based on Photoinduced Electron Transfer," *Angew.Chem. Int. Ed 2004*, pp. 3798-3801.
Product Information, "FAST CAT® (deoxy) Chloramphenicol Acetyltransferase Assay Kits," *Molecular Probes Revised* Jan. 2, 2003, 5 pages.
Product Sheet "Material Safety Data Sheet," *MSDS for F6616* (*Live Technologies*, Revision No. 12, Revision date: May 21, 2010, 3 pages.

Product Sheet, "FAST CAT® Green (Deoxy) Chloramphenicol Acetyltransferase Assay Kit," *Life Technologies 2012*, 5 Pages.
Biswas, T., et al; "Structure of CATI in complex with chloramphenicol"; DOI:10.2210/pdb3u9f/pdb; RCSB Protein Data Bank-3U9F; Deposition: Oct. 18, 2011; Release: Feb. 15, 2012; Last Modified (REVDAT): Apr. 4, 2012; 2 pages; http://www.rcsb.org/pdb/explore/explore.do?structureId=3U9F.
Biswas, T., et al; "Structure of apo-CATI."; DOI:10.2210/pdb3u9b/pdb; RCSB Protein Data Bank-3U9B; Deposition: Oct. 18, 2011; Release: Feb. 15, 2012; Last Modified (REVDAT): Apr. 4, 2012; 2 pages. http://www.rcsb.org/pdb/explore/explore.do?structureId=3U9B.
Crane, B.R., et al; "Murine Inducible Nitric Oxide Synthase Oxygenase Domain (DELTA 114) Complexed With Type I *E. coli* Chloramphenicol Acetyl Transferase and Imidazole."; DOI:10.2210/pdb1noc/pdb; RCSB Protein Data Bank-1NOC; Deposition: Sep. 28, 1997; Release: Oct. 14, 1998; Last Modified (REVDAT); Feb. 24, 2009; 2 pages http://www.rcsb.org/pdb/explore/explore.do?structureId=1NO_C.
Crane, Brian R., et al; "The Structure of Nitric Oxide Synthase Oxygenase Domain and Inhibitor Complexes."; Science, vol. 278, Oct. 17, 1997; pp. 425-431.
Nowicki, H.G.; Studies of Fluorescamine. Part II—Thin-Layer Chromatographic Mobiilitles of Fluorescamine Positive Drugs.; Abstract; Analytical Letters, 2(49); (1979) pp. 1019.
Roidis, A., et al; "Crystal structure of Chloramphenicol acetyltransferase I complexed with Fusidic acid at 2.18 A resolution."; DOI:10.2210/pdb1q23/pdb; RCSB Protein Data Bank-1Q23 Deposition: Jul. 23, 2003; Release: Aug. 3, 2004; Last Modified (REVDAT): Feb. 24, 2009; 2 pages http://www.rcsb.org/pdb/explore/explore.do?structure Id=1Q23.
Roidis, A., et al; "Crystal structure of *E.coli* chloramphenicol acetyltransferase type I at 2.5 Angstrom resolution."; DOI:10.2210/pdb1pd5/pdb; RCSB Protein Data Bank-1PD5; Deposition: May 19, 2003; Release: Jun. 1, 2004; Last Modified (REVDAT): Feb. 24, 2009; 2 pages http://www.rcsb.org/pdb/explore/explore.do?structureId=1PD5.

* cited by examiner

*Primary Examiner* — Nashaat Nashed
(74) *Attorney, Agent, or Firm* — Duane Morris LLP; Siegfried J. W. Ruppert

(57) ABSTRACT

Fast and simple method of detecting the presence of chloramphenicol, a harmful compound if present in food products. The method makes use of a mutant chloramphenicol acetyltransferase (CAT) and a fluorophore-linked chloramphenicol in a system where chloramphenicol and the fluorophore-linked chloramphenicol competes for the active site of the mutant CAT. Because the fluorophore-linked chloramphenicol reduces its fluorescence upon binding to the active site and vice versa increases its fluorescence upon being displaced from the active site by the presence of unmodified chloramphenicol in a sample, the increase of fluorescence caused by a testing sample indicates the presence of chloramphenicol.

31 Claims, 11 Drawing Sheets

FIG. 11

| Primer name | Sequence |
|---|---|
| CAT Nde F | GTAACTCACATGGAGAAAAAAATCACTGGATATACC |
| CAT XhoI R | CATTGACTCGAGTTACGCCCCGCCCTGCCACTC |
| V28W F | GCATTTCAGTCATGGGCTCAAGCTACC |
| V28W R | GGTAGCTTGAGCCCATGACTGAAATGC |
| C31 F | TCAGTTGCTCAAGCGACCTATAACCAG |
| C31 R | CTGGTTATAGGTCGCTTGAGCAACTGA |
| C91 F | AGTGTTCACCCTGCGTACACCGTTTTC |
| C91 R | GAAAACGGTGTACGCAGGGTGAACACT |
| C126 F | CAAGATGTGGCGGCGTACGGTGAAAAC |
| C126 R | GTTTTCACCGTACGCCGCCACATCTTG |
| C196 F | CATCATGCCGTCGCGGATGGCTTCCAT |
| C196 R | ATGGAAGCCATCCGCGACGGCATGATG |
| C212 F | TTACAACAGTACGCCGGATGAGTGGCAG |
| C212 R | CTGCCACTCATCCGCGTACTGTTGTAA |

METHOD AND SYSTEM FOR DETECTION OF CHLORAMPHENICOL

FIELD OF THE INVENTION

The present invention relates to the field of analytic chemistry. More specifically, it relates to a rapid and sensitive method of detecting the presence of a harmful chemical compound in food products.

BACKGROUND OF THE INVENTION

Chloramphenicol is an effective and low-cost antibiotic against different pathogenic bacteria. However, due to the fact that it can cause serious side effects such as, for example, aplastic anaemia, upon ingestion, this antibiotic has been banned from being used in food-producing animals in Canada, United States of America, European Union and many other countries. Nonetheless, chloramphenicol can still be found being improperly used in food production, like fish and honeybee farming, resulting in chloramphenicol contamination in food. Therefore, there is a need for methods which are quick and sensitive in detecting chloramphenicol contamination in food.

SUMMARY OF THE INVENTION

In order to fill the above-mentioned need, the present invention provides a rapid and sensitive method for detecting chloramphenicol. This method using a mutant of the chloramphenicol acetyltransferase (CAT) and a fluorophore-linked chloramphenicol. The mutated enzyme and the fluorophore-labeled ligand retain the ability of specifically binding with each other and, upon such binding, the fluorescence of the fluorophore-linked chloramphenicol is specifically suppressed. Furthermore, the fluorophore-linked chloramphenicol bound on the mutated acetyltransferase can be displaced by an unmodified chloramphenicol upon the presence of the later compound, resulting in an increase in fluorescence.

The fluorophore-linked chloramphenicol is known in the art, for example, U.S. Pat. No. 4,420,568 to Wang et al, Soviet Union Patent No. 392,716 to Nowicki, H. G, *Analytical lettes* 12, 1019-1025, and U.S. Pat. No. 5,262,545 to Haughland et al. However it is unknown that the fluorescence of the linked compound can be modulated by binding of fluorophore-linked chloramphenicol to a biomacromolecule, much less an artificially modified biomacromolecule. The present invention represents the first detection method based on the principle that the fluorescence of the fluorophore-linked chloramphenicol can be strongly suppressed by a modified chloramphenicol acetyltransferase and can be restored by addition of unmodified chloramphenicol. The method of the present invention utilizes such fluorescence changes for the determination of the chloramphenicol concentration. FIG. 2 illustrates the working principle of the method: Mutant of the chloramphenicol acetyltransferase 1 has a reductive amino acid residue 5, acquired through mutation, near the active site. Upon binding to this active site, fluorophore-linked chloramphenicol 2 brings fluorophore 3 close to the reductive amino acid residue 5, which suppresses the fluorescence of the fluorophore. Next, when unmodified chloramphenicol 4 is added to the system, it competes with fluorophore-linked chloramphenicol 2 for the active site on enzyme 1 and, when present in a sufficient amount, chloramphenicol 4 will dislodge fluorophore-linked chloramphenicol 2 from the active site. As a result, its fluorophore is now further away from the reductive residue 5 and its fluorescence is not suppressed any more. The more unmodified chloramphenicol 4 is present, the more fluorophore-linked chloramphenicol 2 is dislodged and the larger increase of fluorescence will be observed. Thus, this method can be used for both qualitative and quantitative measurement of chloramphenicol in a sample.

According to the present invention, the suppression of fluorescence is depending on the following factors:
(1) the nature of the mutation(s) on the CAT,
(2) the type of fluorophore on the fluorophore-linked chloramphenicol, and
(3) the length of the linkage between the fluorophore and chloramphenicol.

It is understood that the specific nature of the mutation, the type of fluorophore and the length of the linkage, however, can be determined by people of ordinary skill in the art and thus are not limitations to the present invention. Rather the specific choices are disclosed herewith as examples for illustrating the present invention. Preferably, the mutation is made on the residue(s) near the active site of CAT, and preferably the mutation is accomplished by replacing the residue(s) with reductive amino acid residues that can reduce the fluorescence of fluorophore on the fluorophore-linked chloramphenicol such as, for example, methionine, tyrosine, and tryptophan.

The specific fluorophore can be chosen with ordinary skill in the art based on the susceptibility of the resulting fluorophore-linked chloramphenicol to fluorescence suppression by reductive amino acid residues such as methionine, tyrosine, and tryptophan. For example, some preferable fluorophores are fluorescein, rhodamine, nitrobenzoxadiazole (NBD), coumarin, dipyrromethenboron difluoride (BODIPY), and their corresponding derivatives.

Similarly, the specific location of mutation and specific replacing amino acid residue(s) can be determined with ordinary skill in the art and their choices are not part of the present invention.

The optimal distance between the fluorophore and the linked chloramphenicol, i.e., the length of the linkage can also be determined with ordinary skill of the art and forms no part of the present invention. Preferably, the length of the linkage should be at least 3 carbon atoms.

Another aspect of this invention is to provide a sensing platform or system for detecting chloramphenicol which comprises a mutated chloramphenicol acetyltransferase and a fluorophore-labeled chloramphenicol of the following general formula:

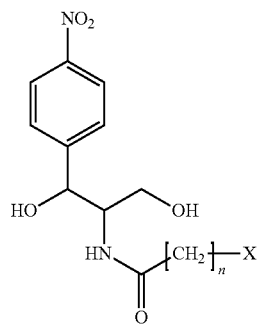

wherein n is not smaller than 3 and x is a fluorophore which can be preferably chosen from fluorescein, rhodamine, nitrobenzoxadiazole (NBD), coumarin, dipyrromethenboron difluoride (BODIPY), and the derivatives of these fluorophores.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

BRIEF DESCRIPTION OF THE DRAWINGS

FIG. 11 lists the sequences of all the primers used in this disclosure. The sequences listed in FIG. 11 are as follows: CAT Nde F (SEQ ID NO: 1), CAT XhoI R (SEQ ID NO: 2), V28W F (SEQ ID NO: 3), V28W R (SEQ ID NO: 4), C31 F (SEQ ID NO: 5), C31 R (SEQ ID NO: 6), C91 F (SEQ ID NO: 7), C91 R (SEQ ID NO: 8), C126 F (SEQ ID NO: 9), C126 R (SEQ ID NO: 10), C196 F (SEQ ID NO: 11), C196 R (SEQ ID NO: 12), C212 F (SEQ ID NO: 13), and C212 R (SEQ ID NO: 14).

DETAILED DESCRIPTION OF PARTICULAR EMBODIMENTS OF THE INVENTION

The Enzyme

The term "chloramphenicol acetyltransferase" refers to a naturally occurring enzyme that can transfer an acetyl group from acetylated co-enzyme A to chloramphenicol or related derivative. The "specifically mutated chloramphenicol acetyltransferase" refers to a particular mutant chloramphenicol acetyltransferase wherein one or more amino acid residue(s) have been changed from the wild type. An example of such specifically mutated chloramphenicol acetyltransferase, as one particular embodiment of the present invention, is V28W of CAT I. It should be emphasized that the present invention is not limited by this CAT I mutant. People of ordinary skill in the art may use other enzymes that are classified into the family of CAT to practice the present invention and bring about a satisfactory result.

As a guideline, any enzyme in the family of CAT which can provide a receptor for receiving a fluorophore-linked chloramphenicol and quenching the fluorescence thereof. Preferably, said receptor's binding affinity should favor unmodified chloramphenicol than the fluorophore-linked chloramphenicol. As another guideline, the amino acid residue used to replace the wild-type residue should preferably be a reductive amino acid residue, typically, for example, tryptophan, tyrosine, and methionine. Further as a guideline, the mutation should be made in a region not more than 15 Å away from the active site of the enzyme. Example of such regions are the ones containing amino acid residues from 22 to 33, from 75 to 80, from 133 to 143, or from 162 to 167.

The Ligand

Figure 1:
FIG. 1 shows the tertiary structure (PDB accession number 1PD5) of the chloramphenicol acetyltransferase I (CAT I).
Figure 2:
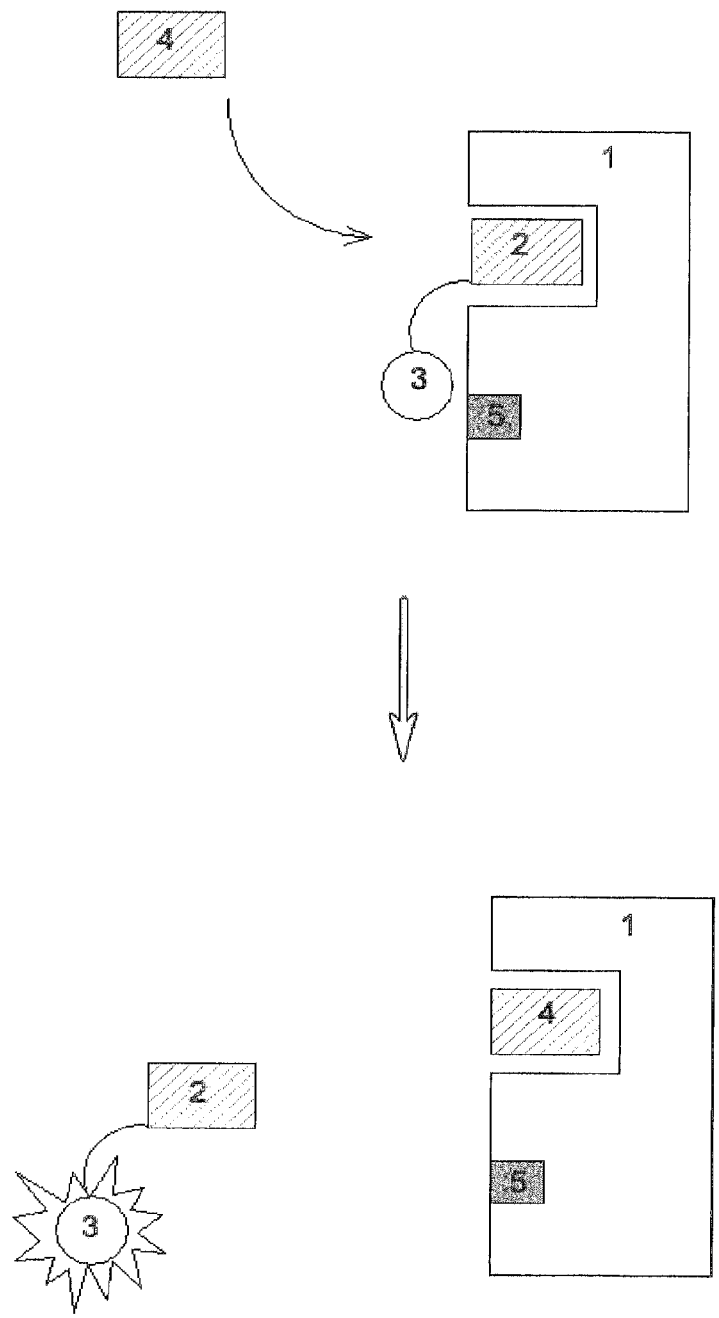
FIG. 2. summarizes the working principle of the present invention.
Figure 3:
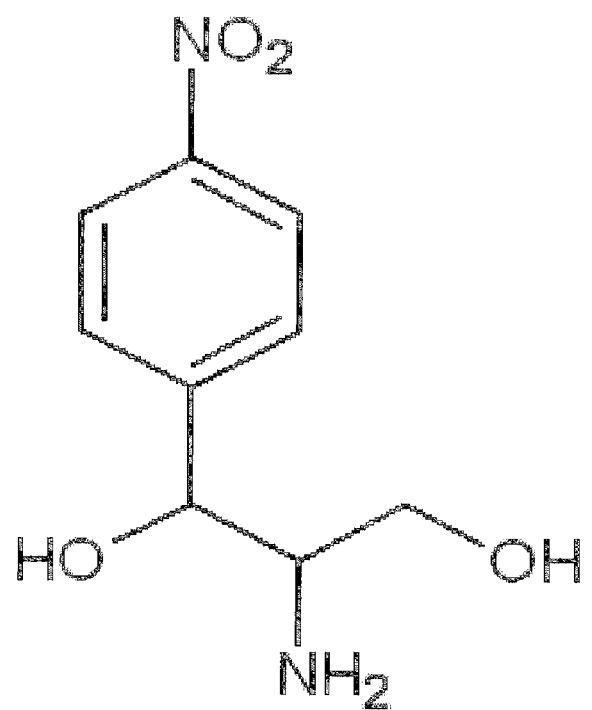
FIG. 3 shows the structure of the chloramphenicol base.

The term "chloramphenicol base" refers to the chemical compound D(−)threo-2-amino-1-(p-nitrophenyl)-1,3-propanediol, whose structure formula is shown in FIG. 3. The term "fluorophore-linked chloramphenicol" refers to the compound that are derivative of the chemical compound D(−) threo-2-amino-1-(p-nitrophenyl)-1,3-propanediol (i.e., chloramphenicol base) that is linked with a fluorophore. Said fluorophore can be fluorescein, rhodamine, coumarin, nitrobenzoxadiazole (NBD), dipyrromethenboron difluoride (BODIPY), or the derivatives of these fluorophores. Of course, people of ordinary skill in the art may use other fluorophore to bring about a satisfactory result in practicing the present invention. As a guideline in practicing the present invention, the fluorophore chosen should be able to interact with a reductive amino acid through photo-induced electron transfer upon binding to the active site of the mutated CAT. It is believed, but not intended to be bound by a theory, that this interaction reduces the fluorescence of the fluorophore-linked chloramphenicol. In the presence of chloramphenicol, this compound will displace the fluorophore-linked chloramphenicol from the active site of the mutated CAT, thus leading to stronger fluorescence as shown in FIG. 2. In order to make the mutated CAT to reduce the fluorescence of the fluorophore-linked chloramphenicol, it is believed that a direct molecular contact between the fluorophore-linked chloramphenicol and the artificially mutated reductive amino acid residue on the CAT is required. This in turn requires an optimal length of the chain linking the fluorophore to chloramphenicol. Preferably, the length of the linking chain is from 7 to 11 atoms, depending on the size and the molecular shape of the fluorophore and its determination is within ordinary skill of the art. The atoms on the linking chain can be carbon, nitrogen, oxygen, phosphorus, or sulfur. Further preferably, the amine group on the chloramphenicol base is linked to carbonyl group to form an amide bond by condensation reaction with carboxyl group or activated carboxyl group.

Particular Embodiments

As particular embodiments of the present invention, the preparation of CAT I V28W mutant, the synthesis of fluorescein-linked chloramphenicol with 9 atoms in the linking chain, and the use of the CAT I mutant and the fluorescein-linked chloramphenicol in detection of chloramphenicol will be described in detail.

Cloning of CAT I V28W

[28] CAT I gene was obtained from E. coli genomic DNA by Polymerase Chain Reaction (PCR) with the use of two primers (CAT Nde F and CAT XhoI R, table 1). The PCR cycling conditions were set as followed: denaturation at 95° C. for 1 min, followed by 35 cycles of amplification at 94° C. for 1 min, 55° C. for 1 min, and lastly extension at 65° C. for 40 s. The PCR product was purified by agarose gel electrophoresis. The purified PCR product and the modified vector pRsetA were digested by NdeI and XhoI restriction enzymes at 37° C. overnight with the following mix up: 5 µl of 10×
restriction enzyme buffer, 1.5 µl NdeI restriction enzyme, 1.5
µl XhoI restriction enzyme and 42 µl purified PCR product (1
µg/µl). The digested fragment was then purified by agarose
gel electrophoresis. The digested CAT I gene and modified
pRsetA were ligated at 4° C. overnight with mix up of 0.5 µl
ligase, 0.5 µl of 50% PEG5000 solution, 1 µl of ligase buffer
(10×), 1.5 µl digested pRsetA and 6.5 µl digested CAT gene.
This ligation product was then transformed to E. coli Top 10
for multiplication. The plasmid was then extracted, purified,
and analyzed by DNA sequencing. The plasmid with success-
fully subcloned CAT I wild-type gene, named as pRsetA-
HisCAT, was selected for V28W mutation.

PCR mutagenesis was used to generate V28W mutant by
using the Quickchange II Site-Directed Mutagenesis Kits. 1
µl of 10 ng/µl of the plasmid pRsetA-HisCAT were mixed
with 1 µl of forward and reverse primer (V28W-F and V28W-
R, table 1), 1 µl dNTPs, (10 mM), 5 µl 10× buffer, and 1 µl
PfuUltra High-Fidelity DNA polymerase. The PCR cycling
conditions were set as followed: denaturation at 95° C. for 1
min, followed by 18 cycles of amplification at 94° C. for 1
min, 58° C. for 1 min, and lastly extension at 68° C. for 3 mins
and 40 s. The PCR product was then digested by 1 µl DpnI
digestion enzyme at 37° C. for 2.5 hrs. After that, the digested
product was transformed to E. coli Top 10. The plasmid was
extracted, purified, and analyzed by DNA sequencing. In
order to raise the protein stability in solution, the 5 free
cysteine (in CAT I V28W are mutated to alanine by PCR
mutagenesis with similar procedure as described, where the
PCR primers are listed in Table I. The successfully mutated
plasmid was named as pRsetA-His CATV28W and trans-
formed into E. coli BL21 (DE3) for overexpression of the
CATI V28W mutant.

Overexpression and Purification of Cat I V28W

A single colony of E. coli. BL21 (DE3) contained pRsetA-
HisCATV28W was inoculated into 5 ml sterilized LB
medium with ampicillin (100 mg/ml). The pre-culture was
incubated at 37° C. overnight shaking with 280 rpm. Then, 2
ml pre-culture was added into 200 ml sterilized 2XTY
medium with ampicillin (100 mg/ml). This culture was incu-
bated at 37° C. shaking with 280 rpm until its OD600 reached
0.7.400 µl filtered IPTG (0.2 M) was added to the culture. The
culture was then further incubated at 37° C. for 4 hrs shaking
with 280 rpm. The cells were harvested in a 500 ml centrifu-
gal bottle by centrifugation with 8000 rpm at 4° C. for 20
mins, and were finally stored at −20° C.

Before purification of the expressed protein, the collected
cells were recompensed in 15 ml solubilization buffer (0.02M
NaH2PO4 with 0.5M NaCl, pH 7.4). 50 µl lysozyme (75
mg/ml) and 10 µl DNase were added to the resuspended cells.
The mixture was incubated at 30° C. water bath for 30 mins.
The mixture was then sonicated in ice by ultrasonic disinte-
grator with a pulse of 30 s for 5 cycles. The bacterial lysate
was subjected into centrifugation with 13000 rpm at 4° C. for
1 hr and 30 mins. The supernatant was collected and filtered
before subjecting to chromatographic purification.

Figure 4:
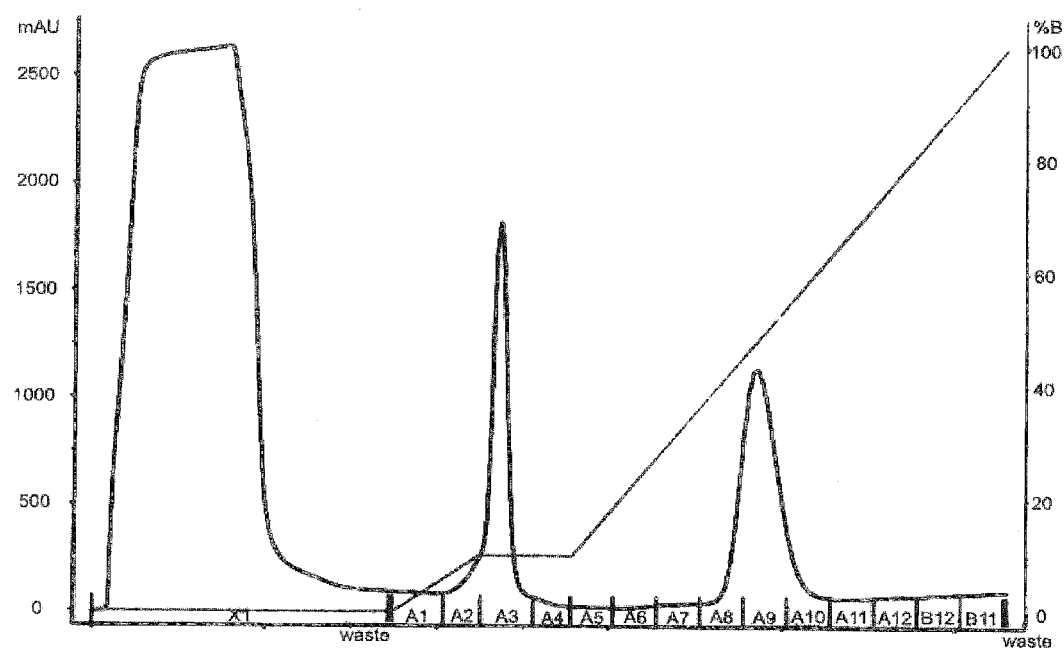
FIG. 4 shows the chromatogram of the nickel-affinity chromatographic purification of the V28W mutant of CAT I. Fraction A8-A10 was the purified CAT I V28W.
Figure 5:
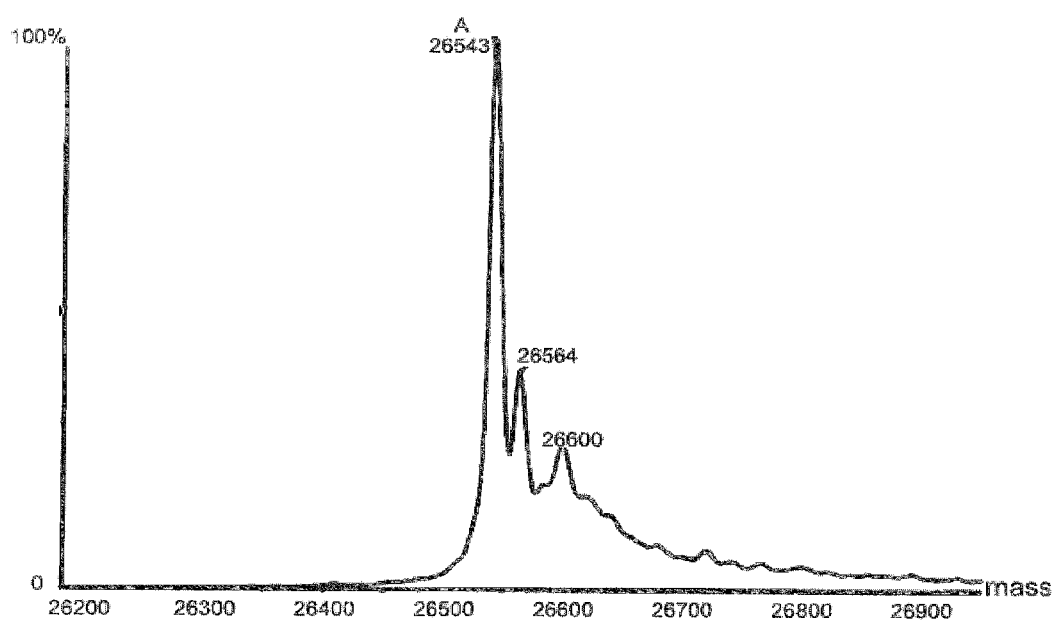
FIG. 5 shows the ESI mass spectrum of the CAT I V28W.

By Fast Protein Liquid Chromatography (FPLC), CAT I
V28W mutants with six histidine-tagged at N terminal were
purified by nickel affinity column. A HiTrap chelating col-
umn with 0.1M NiSO4 loaded was equilibrated with binding
buffer (0.02M NaH2PO4, 0.5M NaCl, pH 7.4) first. Then, the
filtered supernatant sample was injected together with bind-
ing buffer. After that, the mixture was eluted with elution
buffer (0.02M Na H2PO4, 0.5M NaCl, 0.5M Imidazole, pH
7.4) and different fractions were collected. The desired frac-
tion(s) containing purified protein was dialyzed with TSE
buffer (50 mM Tris-HCl, 100 mM NaCl, 0.1 mM EDTA, pH
8.0). As shown in FIG. 4, fractions A8-A10 was the purified
CAT I V28W. The mass spectrum of the CAT I V28W was
obtained and shown in FIG. 5.

Synthesis of Fluorescein-Linked Chloramphenicol

Compound 1:
tert-butyl(6-(((1R,2R)-1,3-dihydroxy-1-(4-nitrophenyl)
propan-2-yl)amino)-6-oxohexyl)carbamate. To a mixture of
0.74 g N-boc-6-aminohexanoic acid, 0.6 g triethylamine, and
0.43 g hydroxybenzotriazole in 50 ml THF was added 0.61 g
1-ethyl-3-(3-dimethylaminopropyl) carbodiimide. The reac-
tion mixture was stirred at room temperature for 30 min. 0.85
g chloramphenicol base was then added and the mixture was
stirred for further 6 hours. The solution was filtered from
precipitate and the filtrate was evaporated on a rotary evapo-
rator. The remained oily liquid was dissolved in 30 ml EtOAc
and washed with 0.05 M HCl (2×15 ml) and saturated sodium
carbonate (2×15 ml). The solution was then dried over
MgSO4, filtered and evaporated. A yield of 0.75 g compound
1 was obtained.

Compound 2:
6-amino-N-((1R,2R)-1,3-dihydroxy-1-(4-nitrophenyl)
propan-2-yl) hexanamide. To a 0.5 g compound 1 was added
1.5 ml trifluoroacetic acid, and the mixture was stirred at
room temperature for 30 min. The excess trifluoroacetic acid
was removed under vacuum and the residue was purified by
flash chromatography (DCM/MeOH, 4:1) to yield 0.15 g of
compound 2.

Compound 3:
5-(3-(6-(((1R,2R)-1,3-dihydroxy-1-(4-nitrophenyl)pro-
pan-2-yl)amino)-6-oxohexyl)thioureido)-2-(6-hydroxy-3-
oxo-3H-xanthen-9-yl)benzoic acid. To a solution of 0.15 g
compound 2 in 10 ml THF was added 60 µl of triethylamine.
The mixture was stirred at room temperature in dark for 20
min before the addition of 0.18 g fluorescein-5-isothiocyan-
ate. The mixture was stirred for 5 hours and concentrated on
a rotary evaporator. The crude product was subjected to flash
chromatography (DCM/MeOH, 6:1) to yield 0.05 g com-
pound 3.

Fluorescence Response of Fluorescein-Linked Chloram-
phenicol

Figure 6:
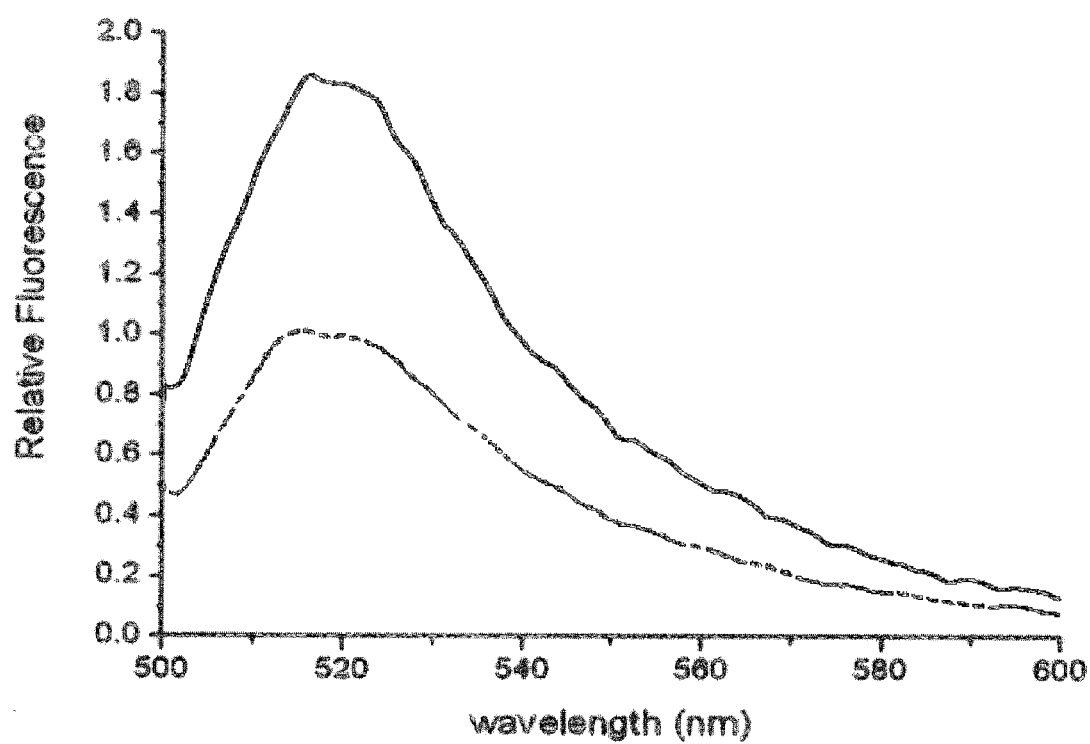
FIG. 6 shows the fluorescent spectra of the 0.15 μM fluorescein-linked chloramphenicol before (solid line) and after (dash dot line) the addition of 1.5 μM CAT I mutant V28W. The excitation wavelength is 494 nm and the slit width is 5 nm.
Figure 7:
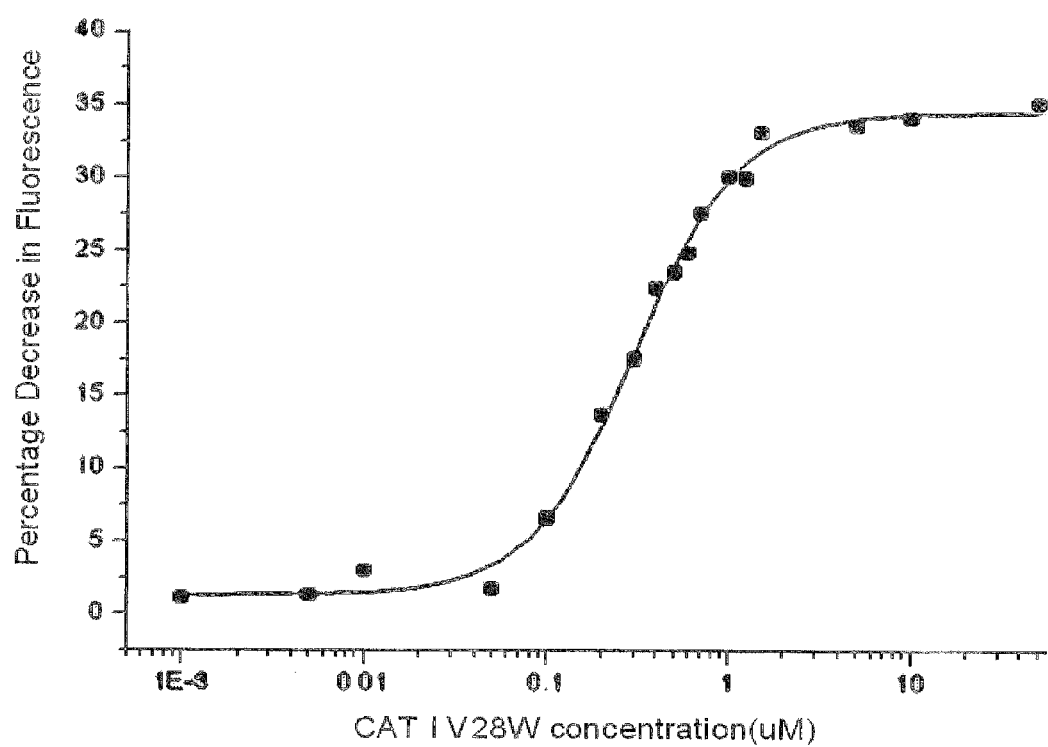
FIG. 7 shows the sigmoidal fluorescent response curves of fluorescein-linked chloramphenicol in the presence of CAT I V28W mutant (concentration from 0.005 μM to 50 μm).

As shown in FIG. 6, the fluorescence of fluorescein-linked
chloramphenicol can be significantly reduced by the CAT I
V28W mutant. To monitor the fluorescence response of fluo-
rescein-linked chloramphenicol in the presence of different
concentrations of CAT I V28W mutant, a fluorescence titra-
tion experiment was performed. Fluorescence measurements
were performed on a Perkin Elmer LS 50B spectrofluorom-
eter with the excitation wavelength set at 494 nm and the
excitation and emission slit width set at 5 nm. The concen-
tration of fluorescein-linked chloramphenicol was 0.15 µM,
and the concentration of CAT I V28W mutant was varied
from 0.001 µM to 50 µM. As shown in FIG. 7, a sigmoidal
fluorescence response curve was obtained when the percent-
age decrease in fluorescence was plotted against the concen-
trations of CAT I V28W.

Detecting the Presence of Chloramphenicol

Figure 8:
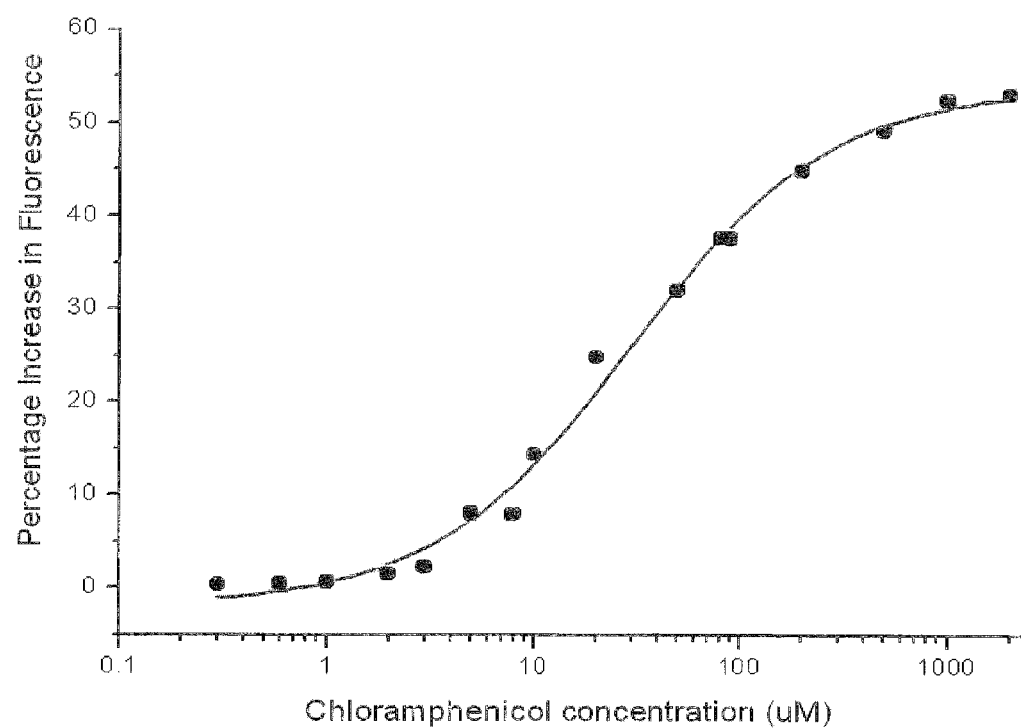
FIG. 8 shows the sigmoidal fluorescent response curves of fluorescein-linked chloramphenicol in the presence of chloramphenicol.

The detection of chloramphenicol contamination in
samples, for example, food samples can be done by monitor-
ing the fluorescent change through the competition of the
active site of CAT I V28W mutant with the fluorescein-linked
chloramphenicol. One testing was performed and the result,
as shown in FIG. 8, demonstrated that this detecting method
is very sensitive. When the presence of chloramphenicol at as
low as 10 µM, about a 10% increase in fluorescence was
observed with this method. The measurement condition is the
same as the fluorescence titration except the CAT I V28W and
the fluorescein-linked chloramphenicol are fixed at 0.15 µM with samples containing various known chloramphenicol concentrations. In real life practice, samples to be tested can be prepared by various conventional methods known to people in the field, which forms no part of this invention. In addition to merely qualitatively determining the presence of chloramphenicol based on an observed increased in fluoresce of the assay system as disclosed here. The curve obtained with a serial of known samples, such as the one shown in FIG. 8, may be used as standard for quantitatively measuring the concentration of chloramphenicol present in an unknown sample. Furthermore, this same method can also be used for detecting derivatives of the chloramphenicol compound as long as such derivatives can compete with the fluorescein-linked chloramphenicol for the active site of the mutant CAT enzyme.

Detecting the Presence of Chloramphenicol in Honey Samples

Chloramphenicol residue in honey can be detected by standard extraction protocol followed by detection using the fluorescein-linked chloramphenicol coupled with CAT I V28W mutant. Firstly, 7×3 g of honey was weighted and known concentration of chloramphenicol (0.1, 1, 10, 50, 100, 1000 and 10000 µM) was added. These chloramphenicol containing honey samples were diluted with 3 ml distilled water. Chloramphenicol in these mixture was extracted by 6 ml ethyl acetate. The aqueous layer and the organic layer were separated using centrifugation (15 min, 3000 g). 4 ml of chloramphenicol containing ethyl acetate was collected and evaporated by rotary evaporation. The remaining oily liquid was then dissolved into 1 ml hexane followed by addition of 0.5 ml TSE buffer.

Figure 9:
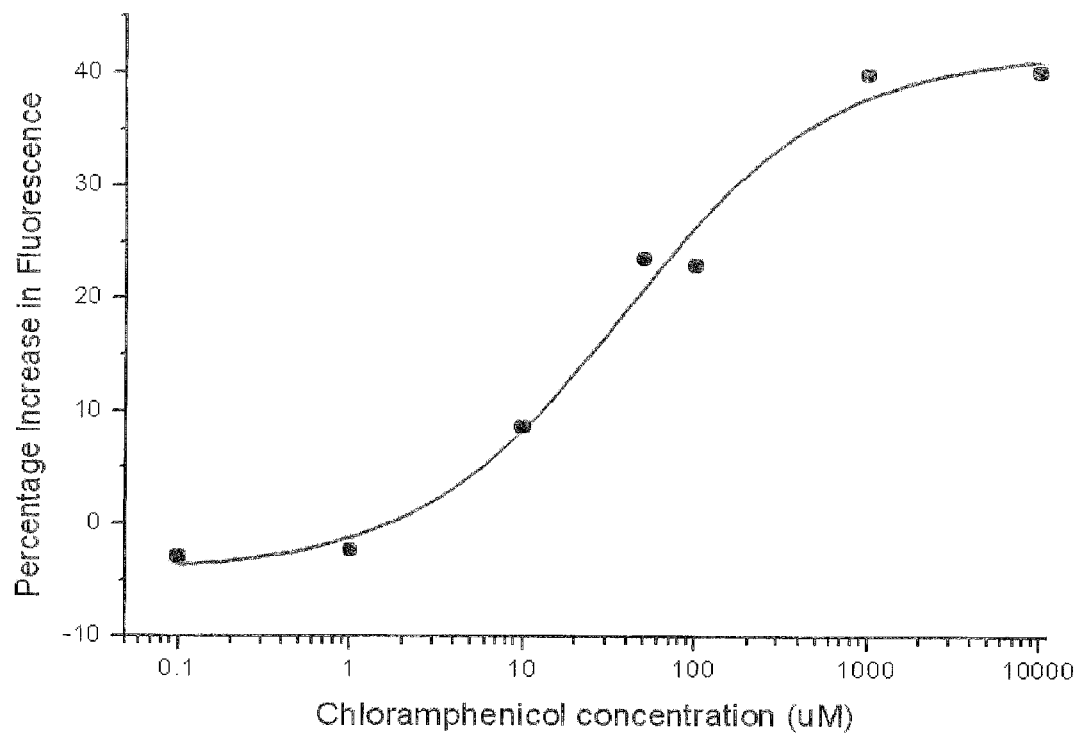
FIG. 9 shows the fluorescent measurement of chloramphenicol in food sample (honey) as an embodiment of the present invention.

The 7 extracted samples in TSE buffer were mixed with 0.3 µM CAT I V28W mutant and 0.3 µM fluorescein-linked chloramphenicol. The fluorescence intensity was measured and plotted against the concentration of chloramphenicol and the result is shown in FIG. 9.

Detecting the Presence of Chloramphenicol in Egg Samples

Figure 10:
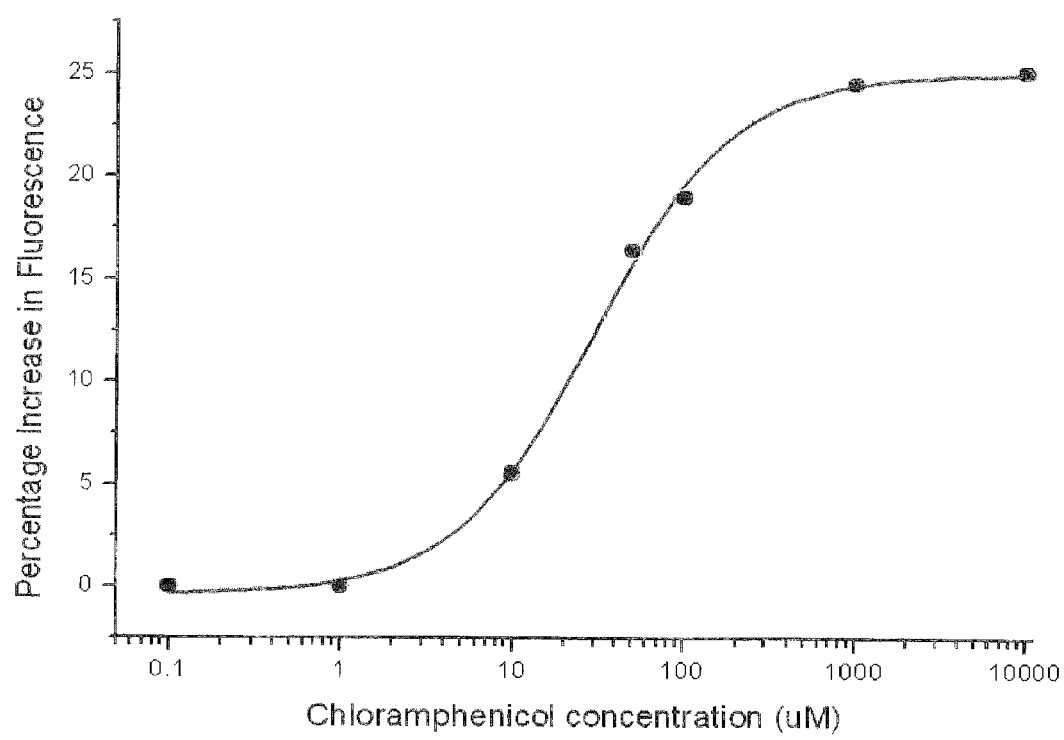
FIG. 10 shows the fluorescent measurement of chloramphenicol in food sample (egg) as another embodiment of the present invention.

Chloramphenicol residue in egg was detected by similar procedures as for honey samples described above, except that 1 g of homogenized egg was directly dissolved into 6 ml ethyl acetate without any dilution, and the fluorescence intensity was plotted against the concentration of chloramphenicol and the result is showed in FIG. 10.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A method for quantitative or qualitative measuring chloramphenicol in a sample, comprising the steps of:
   (a) contacting a mutant chloramphenicol acetyltransferase (CAT)/fluorophore-linked chloramphenicol complex with an amount of a sample to be tested for the presence of chloramphenicol; and
   (b) determining the presence of the chloramphenicol in the sample based on the fluorescence intensity of the fluorophore-linked chloramphenicol after displacement from the mutant CAT/fluorophore-linked chloramphenicol complex by the chloramphenicol present in the sample;
   wherein the mutant CAT comprises at its active site at least one reductive amino acid residue, and
   wherein the reductive amino acid residue suppresses the fluorescence of the fluorophore-linked chloramphenicol when present in the mutant CAT/fluorophore-linked chloramphenicol complex.

2. The method according to claim 1, wherein the reductive amino acid residue is selected from the group consisting of tryptophan, tyrosine, and methionine.

3. The method according to claim 1, wherein the mutant CAT comprises a tryptophan residue at a position corresponding to amino acid position 28 of CAT I from *Escherichia coli*.

4. The method according to claim 1, wherein the fluorophore-linked chloramphenicol is of the formula:

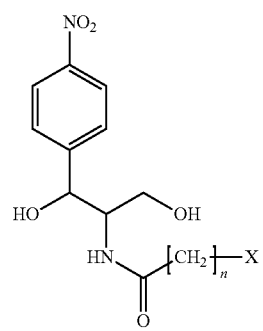

wherein n is not smaller than 3 and x is the fluorophore.

5. The method according to claim 4, wherein the fluorophore is selected from the group consisting of fluorescein, rhodamine, nitrobenzoxadiazole (NBD), coumarin, dipyrromethenboron difluoride (BODIPY), and a derivative thereof.

6. The method according to claim 5, wherein the fluorophore is fluorescein.

7. The method according to claim 4, wherein n is 9.

8. The method according to claim 1, wherein the sample is a food sample.

9. The method according to claim 8, wherein the food sample is honey or egg.

10. The method according to claim 1, wherein the reductive amino acid residue is inserted within an amino acid region of a wild-type CAT and wherein the amino acid region of the wild-type CAT is selected from the group consisting of an amino acid regions region corresponding to *Escherichia coli* CAT 1 amino acid region comprising amino acid residues from 22 to 33, an amino acid region corresponding to *Escherichia coli* CAT 1 amino acid region comprising amino acid residues from 75 to 80, an amino acid region corresponding to *Escherichia coli* CAT 1 amino acid region comprising amino acid residues from 133 to 143, and an amino acid region corresponding to *Escherichia coli* CAT 1 amino acid region comprising amino acid residues from 162 to 167.

11. The method according to claim 1, further comprising the step of contacting the mutant CAT with a fluorophore-linked chloramphenicol to form the mutant CAT/fluorophore-linked chloramphenicol complex.

12. The method according to claim 1, wherein in the mutant CAT a free cysteine residue is mutated.

13. The method according to claim 12, wherein the free cysteine residue is mutated to alanine.

14. The method according to claim 1, wherein the mutant CAT is produced in a prokaryotic cell.

15. The method according to claim 1, wherein the mutant CAT comprises a tag.

16. The method according to claim 15, wherein the tag is a histidine tag.

17. An assay system for detecting or measuring chloramphenicol in a sample, comprising:
(i) a mutant chloramphenicol acetyltransferase (CAT) comprising a reductive amino acid residue at its active site and
(ii) a fluorophore-linked chloramphenicol for binding to the mutant CAT;
wherein the reductive amino acid residue suppresses the fluorescence of the fluorophore-linked chloramphenicol when present in the mutant CAT/fluorophore-linked chloramphenicol complex.

18. The assay system according to claim 17, wherein the reductive amino acid residue is selected from the group consisting of tryptophan, tyrosine, and methionine.

19. The assay system according to claim 17, wherein the CAT comprises a tryptophan residue at a position corresponding to amino acid position 28 of CAT I from *Escherichia coli*.

20. The assay system according to claim 17, wherein the fluorophore-linked chloramphenicol is of the following formula:

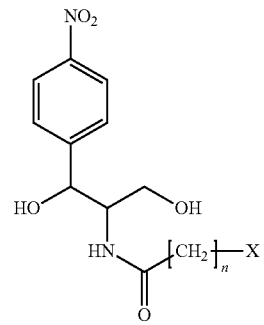

wherein n is not smaller than 3 and x is the fluorophore.

21. The assay system according to claim 20, wherein the fluorophore is selected from the group consisting of fluorescein, rhodamine, nitrobenzoxadiazole (NBD), coumarin, dipyrrometheneboron difluoride (BODIPY), and a derivative thereof.

22. The assay system according to claim 21, wherein the fluorophore is fluorescein.

23. The assay system according to claim 20, wherein n is 9.

24. The assay system according to claim 17, wherein the sample is a food sample.

25. The assay system according to claim 24, wherein the food sample is honey or egg.

26. The assay system according to claim 17, wherein the reductive amino acid residue is inserted within an amino acid region of a wild-type CAT and wherein the amino acid region of the wild-type CAT is selected from the group consisting of an amino acid regions region corresponding to *Escherichia coli* CAT 1 amino acid region comprising amino acid residues from 22 to 33, an amino acid region corresponding to *Escherichia coli* CAT 1 amino acid region comprising amino acid residues from 75 to 80, an amino acid region corresponding to *Escherichia coli* CAT 1 amino acid region comprising amino acid residues from 133 to 143, and an amino acid region corresponding to *Escherichia coli* CAT 1 amino acid region comprising amino acid residues from 162 to 167.

27. The assay system according to claim 17, wherein in the mutant CAT a free cysteine residue is mutated.

28. The assay system according to claim 27, wherein the free cysteine residue is mutated to alanine.

29. The assay system according to claim 17, wherein the mutant CAT is produced in a prokaryotic cell.

30. The assay system according to claim 17, wherein the mutant CAT comprises a tag.

31. The assay system according to claim 30, wherein the tag is a histidine tag.

\* \* \* \* \*

SEQUENCE LISTING

```
<160> NUMBER OF SEQ ID NOS: 14

<210> SEQ ID NO 1
<211> LENGTH: 36
<212> TYPE: DNA
<213> ORGANISM: Artificial Sequence
<220> FEATURE:
<223> OTHER INFORMATION: primer

<400> SEQUENCE: 1
gtaactcaca tggagaaaaa aatcactgga tatacc                               36

<210> SEQ ID NO 2
<211> LENGTH: 33
<212> TYPE: DNA
<213> ORGANISM: Artificial Sequence
<220> FEATURE:
<223> OTHER INFORMATION: primer

<400> SEQUENCE: 2
cattgactcg agttacgccc cgccctgcca ctc                                  33

<210> SEQ ID NO 3
<211> LENGTH: 27
<212> TYPE: DNA
<213> ORGANISM: Artificial Sequence
<220> FEATURE:
<223> OTHER INFORMATION: pimer

<400> SEQUENCE: 3
gcatttcagt catgggctca agctacc                                         27

<210> SEQ ID NO 4
<211> LENGTH: 27
<212> TYPE: DNA
<213> ORGANISM: Artificial Sequence
<220> FEATURE:
```

```
<223> OTHER INFORMATION: primer

<400> SEQUENCE: 4
ggtagcttga gcccatgact gaaatgc                                        27

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5
tcagttgctc aagcgaccta taaccag                                        27

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
ctggttatag gtcgcttgag caactga                                        27

<210> SEQ ID NO 7
<211> LENGTH: 27
<212> TYPE: DNA
<213> ORGANISM: Artificial Sequence
<220> FEATURE:
<223> OTHER INFORMATION: primer

<400> SEQUENCE: 7
agtgttcacc ctgcgtacac cgttttc                                        27

<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8
gaaaacggtg tacgcagggt gaacact                                        27

<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9
caagatgtgg cggcgtacgg tgaaaac                                        27

<210> SEQ ID NO 10
<211> LENGTH: 27
<212> TYPE: DNA
<213> ORGANISM: Artificial Sequence
<220> FEATURE:
<223> OTHER INFORMATION: primer

<400> SEQUENCE: 10
gttttcaccg tacgccgcca catcttg                                        27

<210> SEQ ID NO 11
```

```
<211> LENGTH: 27
<212> TYPE: DNA
<213> ORGANISM: Artificial Sequence
<220> FEATURE:
<223> OTHER INFORMATION: primer

<400> SEQUENCE: 11
catcatgccg tcgcggatgg cttccat                                              27

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
atggaagcca tccgcgacgg catgatg                                              27

<210> SEQ ID NO 13
<211> LENGTH: 27
<212> TYPE: DNA
<213> ORGANISM: Artificial Sequence
<220> FEATURE:
<223> OTHER INFORMATION: primer

<400> SEQUENCE: 13
ttacaacagt acgcggatga gtggcag                                              27

<210> SEQ ID NO 14
<211> LENGTH: 27
<212> TYPE: DNA
<213> ORGANISM: Artificial Sequence
<220> FEATURE:
<223> OTHER INFORMATION: primer

<400> SEQUENCE: 14
ctgccactca tccgcgtact gttgtaa                                              27
```